United States Patent [19]

Johncock

[11] 4,451,645
[45] May 29, 1984

[54] EPOXY COMPOUNDS

[75] Inventor: Peter Johncock, Farnborough, England

[73] Assignee: The Secretary of State for Defence in Her Britannic Majesty's Government of the United Kingdom of Great Britain and Northern Ireland, London, England

[21] Appl. No.: 423,318

[22] Filed: Sep. 24, 1982

[30] Foreign Application Priority Data

Oct. 1, 1981 [GB] United Kingdom ................. 8129618

[51] Int. Cl.³ ...................... C08G 59/28; C08G 59/30; C08G 59/32
[52] U.S. Cl. .................................. 528/391; 528/402; 528/407; 528/418; 549/552
[58] Field of Search ............... 528/391, 407, 402, 418; 549/552

[56] References Cited

U.S. PATENT DOCUMENTS

| | | | |
|---|---|---|---|
| 2,951,822 | 9/1960 | Reinking | 528/418 X |
| 3,449,375 | 6/1969 | Newey | 528/418 X |
| 3,595,882 | 7/1971 | Bremmer | 528/418 X |

*Primary Examiner*—Earl A. Nielsen
*Attorney, Agent, or Firm*—Cushman, Darby & Cushman

[57] ABSTRACT

An epoxy compound includes one or two aromatic rings, one N-diglycidyl group per aromatic ring and one or two halogen or halogen-containing groups per aromatic ring, the epoxy compound having the general formula:

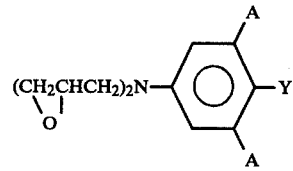

in which Y is selected from A and

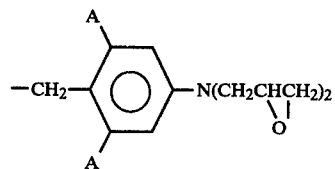

each A being independently selected from halogen, halogen containing group and H, provided that at least one of the groups A per aromatic ring is a halogen or halogen containing group. In any one compound, when A is a hologen or halogen containing group, it is preferred that each A is the same.

When the epoxy compound contains only one aromatic ring the group A may be a polyfluoroalkyl group in which case one or two such groups may be attached to the aromatic ring; or a polyfluoro-alkoxy group, in which case only one such group is attached to the aromatic ring.

When the epoxy compound contains two aromatic rings, the group A may be Cl, Br, or a polyfluoroalkyl group and one or two such groups may be attached to each aromatic ring.

The epoxy compounds may be cured to form high molecular weight polymers with improved resistance to moisture.

22 Claims, No Drawings

EPOXY COMPOUNDS

The present invention relates to epoxy compounds and to epoxy resins made from them.

Epoxy resins are used widely in fiber reinforced composites, in coatings, foams and as adhesives. However epoxies have the disadvantage that they are adversely affected by water. Prolonged exposure to water leads to absorption of moisture by the resin. The moisture acts as a plasticizer lowering the glass transition temperature of the resin. Consequently the maximum service temperature of the resin is lowered when the resin absorbs moisture. In addition, the combined effects of water, temperature and stress can lead to the formation of cracks in the resin with a consequent decrease in mechanical properties. The damaging effects of water on the elevated temperature properties of epoxies prevents their full potential as matrix materials in fiber reinforced composites and as adhesives and coatings being realized.

The present invention provides epoxy compounds that may be cured to form high molecular weight polymers which have improved resistance to moisture.

According to the present invention an epoxy compound includes one or two aromatic rings, one N-diglycidyl group per aromatic ring and one or two halogen or halogen-containing groups per aromatic ring, the epoxy compound having the general formula:

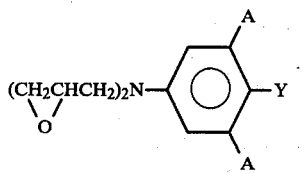

Formula 1 in which Y is selected from A and

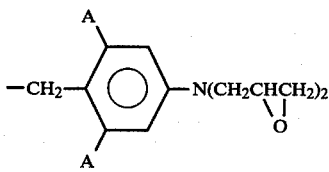

each A being independently selected from halogen, halogen containing group and H, provided that at least one of the groups A per aromatic ring is a halogen or halogen containing group. In any one compound, when A is a halogen or halogen containing group and when more than one A is present, it is preferred that each group A is the same.

Epoxy compounds according to the present invention may include one aromatic ring and only one halogen-containing group as shown in Formula 2.

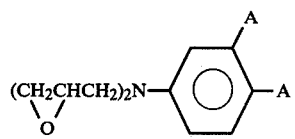

Formula 2 where A is a halogen containing group or H, only one of the groups A being a halogen containing group, which may be a polyfluoroalkyl group $Y(CF_2)_n-$ or a polyfluoroalkoxy group $X(CF_2)_nCH_2O-$ in which X is either H or F and n is an integer between 1 and 10 inclusive. When A is a polyfluoroalkyl group, for example $-CF_3$, it is preferably attached to the aromatic ring at a meta position with respect to the nitrogen atom. When A is a polyfluoroalkoxy group, for example $H(CF_2)_6CH_2O$, it is preferably attached to the aromatic ring at the para position with respect to the nitrogen atom.

Epoxy compounds according to the present invention may include one aromatic ring and two halogen containing groups as shown in Formula 3:

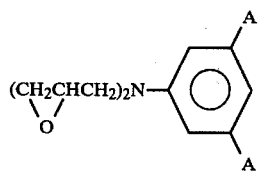

Formula 3 where each A is a halogen containing group which may be a polyfluoroalkyl group $X(CF_2)_n-$ in which X is either H or F and n is an integer between 1 and 10 inclusive. Preferably each A is the same and is preferably a trifluoromethyl group.

Epoxy compounds according to the present invention may include two aromatic rings and one halogen or halogen-containing group per aromatic ring as shown in Formula 4:

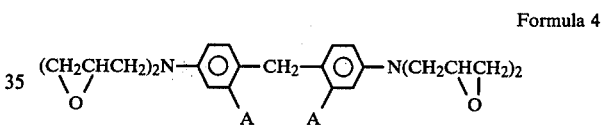

Formula 4 where each A is a halogen or halogen-containing group. Preferably A is chlorine, bromine or a polyfluoroalkyl group $X(CF_2)_n-$ in which X is fluorine or hydrogen and n is an integer between 1 and 10 inclusive. Preferably the polyfluoroalkyl group is $-CF_3$. Preferably each group A is the same.

Epoxy compounds according to the present invention may include two aromatic rings and two halogen or halogen-containing groups per aromatic ring as shown in Formula 5:

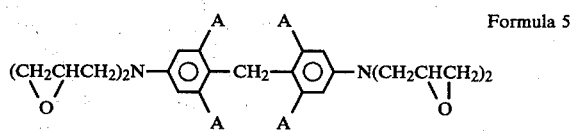

Formula 5 where each A is a halogen or halogen-containing group. A is preferably chlorine, bromine or a polyfluoroalkyl group $(X(CF_2)_n-$ in which X is fluorine or hydrogen and n is an integer between 1 and 10 inclusive. It is preferred that the polyfluoroalkyl group is $-CF_3$. Preferably each group A is the same.

The preferred embodiments of the present invention are 3-(trifluoromethyl)-N,N-bis(2,3-epoxypropyl)aniline (Formula 6), 4-(1,1,7-trihydryl-F-heptyloxy-N,N-bis(2,3-epoxypropyl)aniline (Formula 7), bis[2-(trifluoromethyl)-4-bis(2,3-epoxypropyl)aminophenyl]methane (Formula 8), bis [2-chloro-4-bis(2,3-epoxypropyl)aminophenyl]methane (Formula 9), bis[2-bromo-4- bis(2,3-epoxypropyl)aminophenyl]methane (Formula 10), bis[2,6-chloro, -4-bis(2,3-epoxypropyl)aminophenyl]methane (Formula 11) and 3,5-bis(trifluoromethyl)-N,N-bis(2,3-epoxypropyl)aniline (Formula 12).

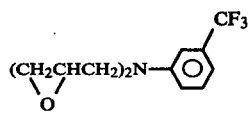
Formula 6

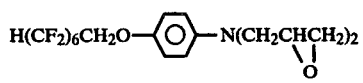
Formula 7

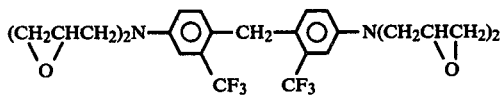
Formula 8

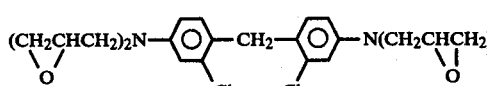
Formula 9

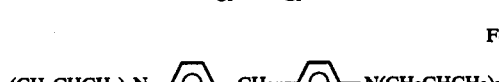
Formula 10

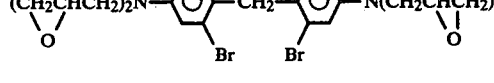
Formula 11

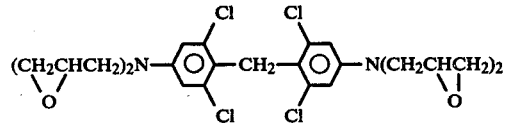
Formula 12

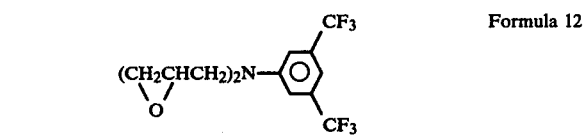

Epoxy compounds of the present invention and according to Formulas 2 and 3 may be prepared by reaction between a parent aniline compound and epichlorhydrin to form a dichlorohydrin intermediate which is then dehydrochlorinated to form an epoxy compound. By parent aniline compound is meant the aniline compound which includes the halogen-containing group or groups desired in the epoxy compound being made, such group or groups being located at the appropriate positions on the aromatic ring. Reaction between epichlorhydrin and a parent aniline may be conducted in a neutral solvent. When the parent aniline contains a polyfluoroalkoxy substituent in the para position the reaction with epichlorhydrin proceeds readily. However a suitable catalyst may be required when the parent aniline contains a polyfluoroalkyl substituent in a meta position, as for example in the preparation of 3-(trifluoromethyl)-N,N-bis(2,3-epoxypropyl)aniline, where the parent aniline, 3-(trifluoromethyl)aniline does not readily form a dichlorohydrin intermediate. The choice of catalyst is important since whereas for example the strong acid catalyst trifluoromethane sulphonic acid promotes the formation of a dichlorohydrin intermediate, the weaker acid catalyst trifluoroacetic acid favours the formation of a monochlorohydrin compound.

Excess epichlorhydrin may be distilled off prior to dehydrochlorination. The latter may be carried out by the action of sodium hydroxide solution in the presence of a phase transfer catalyst such as benzyltriethylammonium chloride and may be allowed to proceed at room temperature.

The epoxy compounds of the present invention and according to Formulas 2 and 3 may also be prepared by the method described in U.S. Pat. No. 3,449,375 in which acetic acid is used as the reaction solvent.

The parent anilines for 4-($\alpha,\alpha,\omega$-trihydril-F-alkoxy)-N,N-bis(2,3 epoxy propyl)anilines are 4-($\alpha,\alpha,\omega$-trihydril-F-alkoxy)anilines which may be prepared from 4-fluoronitrobenzene and $\alpha,\alpha,\omega$-trihydril-F-alkanols. The reaction may be carried out in sodium hydroxide solution in the presence of benzyltriethyl-ammonium chloride, the product being 4-($\alpha,\alpha,\omega$-trihydryl-F-alkoxy)nitrobenzene which may be reduced with hydrogen in the presence of 10% palladium on charcoal to give the appropriate aniline compound.

Epoxy compounds of the present invention and according to either Formula 4 or Formula 5 may be prepared by reaction between a parent aniline compound (as hereinbefore defined) with epichlorhydrin to produce a dichlorohydrin intermediate which is then reacted with a carbonyl compound, the product of which is dehydrochlorinated to an epoxy compound.

The formation of the dichlorohydrin intermediate and dehydrochlorination may be carried out as previously described. Reaction of the dichlorohydrin intermediate with a carbonyl compound may be carried out in the presence of an acid, for example concentrated hydrochloric acid and preferably after excess epichlorhydrin has been distilled off. The choice of carbonyl compound depends on the epoxy compound being made. The reaction may be aided by raising the temperature and it is preferable to allow the reaction to cool prior to dehydrochlorination.

Epoxy compounds of the present invention may be cured to form high molecular weight polymers by conventional techniques using conventional curing agents for example bis(4-aminophenyl)sulphone, bis(4-aminophenyl)methane and 1,3-diaminobenzene. An epoxy compound according to the present invention may be cured on its own, or combined in a mixture of other epoxy compounds and the mixtured cured. Such a mixture may include two or more epoxy compounds of the present invention, and one or more known epoxy compounds. Any such mixture may be tailored to the requirements of the end use to which the cured epoxy is to be put.

High molecular weight epoxy resins made from epoxy compounds of the present invention have improved resistance to water and are less susceptible to water induced impairment of performance.

Reinforced composite materials may be made with suitable reinforcing materials by known techniques, using the epoxy compounds of the present invention in any of the above combinations to form the polymer matrix.

Embodiments of the present invention will now be described by way of example.

EXAMPLE 1

Preparation of 3-(trifluoromethyl)-N,N-bis(2,3-epoxypropyl)aniline

A solution of 3-(trifluoromethane)aniline (48.3 g) and trifluoromethane sulphonic acid (2 g) in benzene was prepared. To this solution was added 110 g epichlorhydrin and the whole was stirred and heated at about 70° C. for about 24 hours. The product was cooled to about 10°–15° C. and 2 g of benzyltriethylammonium chloride was added, followed by a solution consisting of 60 g of sodium hydroxide in 75 g of water. The reaction was allowed to proceed at about room temperature. The mixture was finally heated at about 70° C. for ½ hour. Water was then added and the product extracted with ether. Distrillation gave 41 g of 3-(trifluoromethyl)-N,N-bis(2,3-epoxypropyl)aniline, having a boiling point of 109°–111° C./0.07 Torr.

EXAMPLE 2

Preparation of 4-(1,1,7-trihydryl-F-heptyloxy)aniline

A solution of sodium hydroxide (7.1 g) in water (7.1 g) and benzyltriethylammonium chloride (0.4 g) was added to a mixture of 4-fluoronitrobenzene (14.1 g) and 1,1,7-trihydryl-F-heptanol (36 g). The whole was stirred and heated at about 60° C. for about 6 hours. The product was recrystallized from an ethanol/petroleum ether mixture to give 4-(1,1,7-trihydryl-F-hepyloxy) nitrobenzene (37.2 g), having a melting point of 51°–53° C.

A solution of the product (15.0 g) in ethanol (100 g) was reduced with hydrogen in the presence of 10% palladium on charcoal (0.3 g) to give, after distillation under reduced pressure 4-(1,1,7-trihydryl-F-heptyloxy)aniline (11.7 g), having a melting point of 29°–31° C.

EXAMPLE 3

Preparation of 4-(1,1,7-trihydryl-F-heptyloxy)-N,N-bis(2,3-epoxypropyl)aniline Epichlorhydrin (36.3 g) was added to a stirred solution of 4-(1,1,7-trihydryl-F-heptyloxy)aniline (56 g) in benzene (62 g) and water (9 g) and the mixture was heated at a reflux temperature for about 48 hours. The product was cooled to about 10°–15° C. and benzyltriethylammonium chloride (1 g) was added, followed by a solution of sodium hydroxide (23 g) in water (23 g). After about 20 hours at about room temperature was added and the product extracted with ether. Molecular distillation gave 4-(1,1,7-trihydryl-F-heptyloxy)-N,N-bis(2,3-epoxypropyl)aniline (55.2 g).

EXAMPLE 4

Preparation of bis[2-(trifluoromethyl)-4-bis(2,3-epoxypropyl)aminophenyl]methane Epichlorhydrin (74 g) was added to 3-(trifluoromethyl) aniline (16.1 g) in glacial acetic acid (10.6 g) and the mixture was stirred at a temperature of about 110° C. for about 2½ hours. Excess epichlorhydrin was distilled off under reduced pressure. Water (20 cm$^3$), concentrated hydrochloric acid (10.3 g) and formaldehyde (4.4 g of 37% wt/wt solution) were added to the residue and the mixture was stirred at a temperature of about 100° C. for 18 hours. It was then cooled to about 60° C. and benzyltriethylammonium chloride (0.3 g), followed by sodium hydroxide (24 g) in water (56 g) were added. After 10 minutes the aqueuous layer was decanted and the product again treated with benzyltriethylammonium chloride (0.3 g) and sodium hydroxide (12 g) in water (28 g) to effect complete dehydrochlorination. After about 2½ hours, at about 65° C., 100 cm$^3$ water were added and the product extracted with ether.

After removing the solvent, the product was purified by preparative high performance liquid chromatography (HPLC) to give 10.0 g of bis[2-(trifluoromethyl)-4-bis 2,3-epoxypropyl) aminophenyl]methane.

EXAMPLE 5

Preparation of [bis 3,5-dichloro-4-bis(2,3-epoxypropyl)aminophenyl]methane.

Epichlorhydrin (74 g) was added to 3,5-dichloroaniline (16.2 g) in glacial acetic acid (10.6 g) and the mixture stirred at about 90° C. for about 4½ hours. Excess epichlorhydrin was distilled off under reduced pressure. Water (20 cm$^3$), concentrated hydrochloric acid (10.3 g, weight per cm$^3$ 1.18) and formaldehyde (5.0 g of 37% wt/wt aqueous solution) were added to the residue and the mixture stirred at about 96° C. for about 9½ hours. The solution was cooled and benzyltriethylammonium chloride (0.3 g), benzene (100 cm$^3$) and aqueous sodium hydroxide (80 cm$^3$ of 30% wt/vol) were added. After about 10 minutes at about 50° C., the aqueous layer was decanted and the product again treated with benzyltriethylammonium chloride (0.3 g) and aqueous sodium hydroxide (80 cm$^3$ of 30% wt/vol) at about 65° C. for about 90 minutes to effect complete dehydrochlorination. The organic layer was separated and after removal of solvent it was purified by HPLC techniques to give pure bis[3,5-dichloro-4-bis(2,3-epoxypropyl)aminophenyl]methane (13.7 g).

EXAMPLE 6

Preparation of bis[3-chloro-4-bis(2,3-epoxypropyl)aminophenyl]methane

Epichlorhydrin (74 g) was added to 3-chloroaniline (12.75 g) in glacial acetic acid (10.6 g) and the mixture stirred at 95° C. for about 1½ hours. Excess epichlorhydrin was distilled off under reduced pressure. Water (20 cm$^3$), concentrated hydrochloric acid (10.3 g wt per cm$^3$ 1.18) and formaldehyde (5.0 g of 37% wt/wt aqueous solution) were added to the residue and the mixture stirred at about 85° C. for about 4 hours. The solution was cooled and benzyltriethylammonium chloride (0.3 g) benzene (100 cm$^3$) and aqueous sodium hydroxide (80 cm$^3$ of 30% weight/vol) were added. After about 5 minutes at about 50° C., the aqueous layer was decanted and the organic layer treated three times with benzyltriethylammonium chloride (0.2 g) and aqueous solution hydroxide (40 cm$^3$ of 30% wt/vol solution) at about 75° C. for about ½ hour, 1 hour and 1½ hours respectively, to effect complete dehydrochlorination. The organic layer was separated and after solvent removal it was purified by HPLC techniques to give pure bis[3-chloro-4-bis(2,3-epoxypropyl)aminophenyl]methane (15.1 g).

EXAMPLE 7

Preparation of bis[3-bromo-4-bis(2,3-epoxypropyl)aminophenyl]methane

Epichlorhydrin (74 g) was added to 3-bromoaniline (17.2 g) in glacial acetic acid (10.6 g) and the mixture stirred at about 88° C. for about 5 hours. The excess epichlorhydrin was distilled off under reduced pressure and to the residue were added water (20 cm³), concentrated hydrochloric acid (10.3 g, wt/cm³ 1.18) and formaldehyde (5 g of 37% wt/vol aqueous solution). The mixture was stirred at about 76° C. for about 17 hours. To the cooled solution benzyltriethylammonium chloride (0.3 g), benzene (100 cm³) and sodium hydroxide (80 cm³ of 30% wt/vol aqueous solution) were added. After about 10 minutes at about 50° C. the aqueous layer was decanted, and the organic layer again treated with benzyltriethylammonium chloride (0.3 g) and sodium hydroxide (80 cm³ of 30% wt/vol aqueous solution) at about 75° C. for about 1½ hours to effect complete dehydrochlorination. The organic layer was separated and after removal of solvent, purified by HPLC techniques to give 18.4 g of pure bis[3-bromo-4-bis(2,3-epoxypropyl)aminophenyl]methane.

EXAMPLE 8

A solution of 3,5-bis(trifluoromethyl)aniline (22.9 g) and epichlorohydrin (37 g) in glacial acetic acid (10.6 g) were heated at about 100° C. for about 11 hours. Excess epichlorohydrin was distilled off under reduced pressure. Benzene (100 cm³), a solution of sodium hydroxide (8 g) in water (30 cm³) and benzyltriethylammonium chloride (0.3 g) was added to the residue and the mixture stirred at about room temperature for about 15 minutes, followed by 15 minutes at about 60° C. The aqueous layer was discarded. The dehydrochlorination procedure was repeated three times in order to effect complete conversion. The solvent was removed and the product was purified by preparative high performance liquid chromatography to give 19.5 g of 3,5-bis(trifluoromethyl)-N,N-bis(2,3-epoxypropyl)aniline.

EXAMPLE 9

Epoxy resin castings of approximately 0.025 cm thickness were prepared from the epoxy compounds prepared in Example 1 and Examples 3 to 8, using amine hardeners under the following conditions:

a. 1,3-diaminobenzene (stoichiometric amount based on epoxy equivalent), 16 hours at 80° C., followed by 6 hours at 160° C.
b. Bis(4-aminophenyl)sulphone (60% stoichiometric amount based on epoxy equivalent, 1 hour at 150° C., followed by 5 hours at 180° C.
c. 1,3-diaminobenzene (75% of stoichiometric amount based on epoxy equivalent), 16 hours at 80° C. followed by 6 hours at 160° C.

Known epoxy compounds and mixtures of known epoxy compounds and epoxy compounds of the present invention were cured in the same conditions. Water absorption tests were carried out on the castings in water at 20° C. at $\sqrt{t/d}=200$ (time t in days and thickness d in cm). Water absorption was not Fickian and did not reach a constant value, but continued to increase very slowly with time.

The results of the water absorption tests are given in Table 1.

TABLE 1

| Epoxy Compound | Amine and cure | Water Absorption (w %) of resin |
|---|---|---|
| N,N—bis(2,3-epoxypropyl)aniline (I) | A | 4.5 |
| 3-(trifluoromethyl)-N,N—bis(2,3-epoxypropyl)aniline (II) | A | 2.7 |
| 4-(1,1,7-trihydryl-F-hepytoxy)-N,N—bis(2,3-epoxypropyl)aniline (III) | A | 1.2 |
| tetraglycidyl ether of bis(4-aminophenyl)methane (IV) | A | 7.2 |
| (IV) and (II) (1:1 by weight) | A | 4.5 |
| (IV) and (II) (2:1 by weight) | A | 5.3 |
| (IV) and (III) (1:1 by weight) | A | 3.8 |
| (IV) and (III) (2:1 by weight) | A | 4.9 |
| diglycidyl ether of 2,2-bis(4-hydroxyphenyl)propane (V) | A | 3.5 |
| (V) and (II) (1:1 by weight) | A | 3.1 |
| (IV) | B | 5.6 |
| bis[2-chloro-4-bis(2,3-epoxypropyl)aminophenyl]methane (VI) | B | 3.8 |
| bis[2-bromo-4-bis(2,3-epoxypropyl)aminophenyl]methane (VII) | B | 3.2 |
| bis[2-(trifluoromethyl)-4-bis(2,3-epoxypropyl)aminophenyl]methane (VIII) | B | 2.9 |
| bis[2,6-chloro-4-bis(2,3-epoxypropyl)aminophenyl]methane (IX) | B | 2.9 |
| 3,5-bis(trifluoromethyl)-N,N—bis(2,3-epoxypropyl)aniline (X) | C | 1.6 |
| N,N,—bis(2,3-epoxypropyl)aniline (I) | C | 4.0 |

Comparison between the water absorption figures for the cured epoxy compounds of the present invention (II, III, VI, VII, VIII, IX, X on Table 1) and those for cured known epoxy compounds (I, IV, V in Table 1) show that the cured epoxy compounds of the present invention have superior resistance to water than cured known epoxy compounds. When known epoxies were mixed with epoxies of the present invention and the mixtures cured, the resistance to water of the mixtures was superior to the water resistance of the cured known epoxies alone.

I claim:

1. An epoxy compound including one or two aromatic rings, one N-diglycidyl group per aromatic ring and one or two halogen or polyfluoroalkyl or polyfluoroalkoxy groups per aromatic ring, the epoxy compound having the general formula:

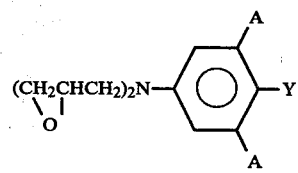

in which Y is selected from A and

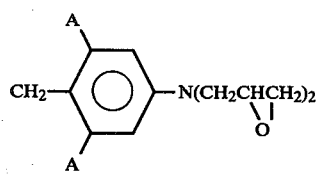

each A being independently selected from halogen, a polyfluoroalkyl group, or a polyfluoroalkoxy group and H, at least one of the groups A per aromatic ring being a halogen, a polyfluoroalkyl or a polyfluoroalkoxy group.

2. An epoxy compound as claimed in claim 1 wherein the epoxy compound includes only one aromatic ring and only one polyfluoroalkyl or polyfluoroalkoxy group, the epoxy compound, having the general formula:

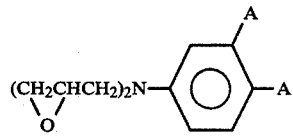

in which A is a polyfluoroalkyl group, a polyfluoroalkoxy group or H, at least one group A being a polyfluoroalkyl or polyfluoroalkoxy group.

3. An epoxy compound as claimed in claim 2 wherein group A is a polyfluoroalkyl group $(X(CF_2)_n-$ in which X is either F or H and n is an integer between 1 and 10 inclusive, the polyfluoroalkyl group being attached to the aromatic ring at a meta position with respect to the nitrogen atom.

4. An epoxy compound as claimed in claim 2 wherein group A is a polyfluoroalkoxy group $X(CF_2)_nCH_2O-$ in which X is either F or H and n is an integer between 1 and 10 inclusive, the polyfluoroalkoxy group being attached to the aromatic ring at the para position with respect to the nitrogen atom.

5. An epoxy compound as claimed in claim 3 wherein the epoxy compound is 3-(trifluoromethyl)-N,N-bis(2,3-epoxypropyl)aniline.

6. An epoxy compound as claimed in claim 4 wherein the epoxy compound is 4-(1,1,7-trihydryl-F-heptyloxy)-N,N-bis(2,3-epoxypropyl)aniline.

7. An epoxy compound as claimed in claim 1 wherein the epoxy compound includes one aromatic ring and two polyfluoroalkyl groups, the epoxy compound having the general formula:

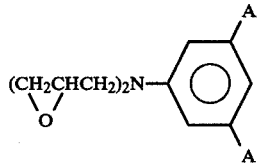

is which A is a polyfluoroalkyl group.

8. An epoxy compound as claimed in claim 7 wherein the polyfluoroalkyl group is $X(CF_2)_n-$, in which X is either F or H, and n is an integer between 1 and 10 inclusive.

9. An epoxy compound as claimed in claim 8 wherein the epoxy compound is 3,5-bis(trifluoromethyl)-N,N-bis(2,3-epoxy propyl)aniline.

10. An epoxy compound as claimed in claim 1 wherein the epoxy compound includes two aromatic rings and one halogen or polyfluoroalkyl group per aromatic ring, the epoxy compound having the general formula:

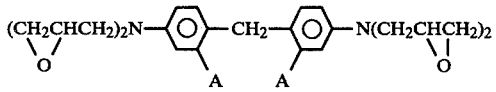

in which A is a halogen or a polyfluoroalkyl group.

11. An epoxy compound as claimed in claim 10 wherein group A is a polyfluoroalkyl group $X(CF_2)_n-$, in which X is either F or H, and n is an integer between 1 and 10 inclusive.

12. An epoxy compound as claimed in claim 10 wherein the epoxy compound is bis[2-chloro-4-bis(2,3-epoxypropyl)aminophenyl]methane.

13. An epoxy compound as claimed in claim 10 wherein the epoxy compound is bis[2-bromo-4-bis(2,3-epoxypropyl)aminophenyl]methane.

14. An epoxy compound as claimed in claim 11 wherein the epoxy compound is bis[2-(trifluoromethyl)-4-bis(2,3-epoxypropyl)aminophenyl]methane.

15. An epoxy compound as claimed in claim 1 wherein the epoxy compound includes two aromatic rings and two halogen or polyfluoroalkyl groups per aromatic ring, the epoxy compound having the general formula:

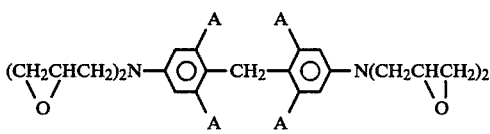

in which A is a halogen or polyfluoroalkyl group.

16. An epoxy compound as claimed in claim 15 wherein group A is a polyfluoroalkyl group $X(CF_2)_n-$, in which X is F or H, and n is an integer between 1 and 10 inclusive.

17. An epoxy compound as claimed in claim 16 wherein the polyfluoroalkyl group is $-CF_3$.

18. An epoxy compound as claimed in claim 15 wherein the group A is bromine.

19. An epoxy compound as claimed in claim 15 wherein the epoxy compound is bis[2,6-chloro,-4-bis(2,3-epoxypropyl)aminophenyl]methane.

20. An epoxy resin including a cured epoxy compound as claimed in claim 1.

21. An epoxy resin including a cured mixture of epoxy compounds including at least one epoxy compound as claimed in claim 1.

22. An epoxy resin including at least one cured epoxy compound as claimed in claim 1 wherein the resin is a matrix of a fibre reinforced composite.

* * * * *

REEXAMINATION CERTIFICATE (388th)
United States Patent [19]
Johncock

[11] B1 4,451,645

[45] Certificate Issued  Sep. 10, 1985

[54] EPOXY COMPOUNDS

[75] Inventor: Peter Johncock, Farnborough, England

[73] Assignee: The Secretary of State for Defence in Her Britannic Majesty's Government of the United Kingdom of Great Britain and Northern Ireland, London, England

Reexamination Request:
No. 90/000,705, Jan. 4, 1985

Reexamination Certificate for:
Patent No.: 4,451,645
Issued: May 29, 1984
Appl. No.: 423,318
Filed: Sep. 24, 1982

[30] Foreign Application Priority Data

Oct. 1, 1981 [GB] United Kingdom ............. 8129618

[51] Int. Cl.³ .................... C08G 59/28; C08G 59/30; C08G 59/32
[52] U.S. Cl. .................... 528/391; 528/402; 528/407; 528/418; 549/552
[58] Field of Search ............. 528/391, 402, 407, 418; 549/552

[56]  References Cited
U.S. PATENT DOCUMENTS

| | | | |
|---|---|---|---|
| 2,951,822 | 9/1960 | Reinking | 528/418 X |
| 3,449,375 | 6/1969 | Newey | 528/418 X |
| 3,595,882 | 7/1971 | Bremmer | 528/418 X |

OTHER PUBLICATIONS

*Chemical Abstracts,* CA 25238 r, vol. 76, 1972, p. 367.
*Chemical Abstracts,* CA 146080d, vol. 79, 1973, p. 290.

*Primary Examiner*—Earl A. Nielsen

[57]  ABSTRACT

An epoxy compound includes one or two aromatic rings, one N-diglycidyl group per aromatic ring and one or two halogen or halogen-containing groups per aromatic ring, the epoxy compound having the general formula:

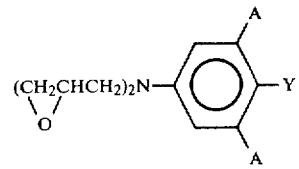

in which Y is selected from A and

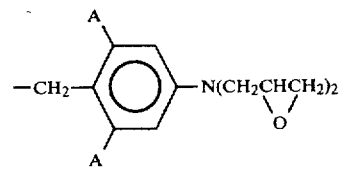

each A being independently selected from halogen, halogen containing group and H, provided that at least one of the groups A per aromatic ring is a halogen or halogen containing group. In any one compound, when A is a halogen or halogen containing group, it is preferred that each A is the same.

When the epoxy compound contains only one aromatic ring the group A may be a polyfluoroalkyl group in which case one or two such groups may be attached to the aromatic ring; or a polyfluoro-alkoxy group, in which case only one such group is attached to the aromatic ring.

When the epoxy compound contains two aromatic rings, the group A may be Cl, Br, or a polyfluoroalkyl group and one or two such groups may be attached to each aromatic ring.

The epoxy compounds may be cured to form high molecular weight polymers with improved resistance to moisture.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-4, 8, 10, 11 and 16-18 are cancelled.

Claims 5-7, 9, 12-15 and 20-22 are determined to be patentable as amended.

Claim 19, dependent on an amended claim, is determined to be patentable.

New claims 23-27 are added and determined to be patentable.

5. An epoxy compound as claimed in claim [3] *7* wherein the epoxy compound is 3-(trifluoromethyl)-N,N-bis(2,3-epoxypropyl)aniline.

6. An epoxy compound as claimed in claim [4] *23* wherein the epoxy compound is 4-(1,1,7-trihydryl-F-heptyloxy)-N,N-bis(2,3-epoxypropyl)aniline.

7. An epoxy compound [as claimed in claim 1 wherein the epoxy compound includes one aromatic ring and two polyfluoroalkyl groups, the epoxy compound] having the general formula:

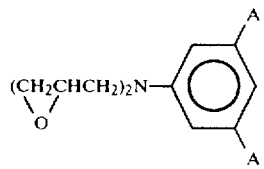

[is] *in* which *each* A is a *group independently selected from hydrogen and $A_1$, where $A_1$ represents a polyfluoroalkyl group $X(CF_2)_n$, where X is H or F and n is an integer in the range of 1 and 10, provided that at least one group A is $A_1$.*

9. An epoxy compound as claimed in claim [8] *7* wherein the epoxy compound is 3,5-bis(trifluoromethyl)-N,N-bis(2,3-epoxy propyl)aniline.

12. An epoxy compound as claimed in claim [10] *15* wherein the epoxy compound is bis[2-chloro-4-bis(2,3-epoxypropyl)aminophenyl]methane.

13. An epoxy compound as claimed in claim [10] *15* wherein the epoxy compound is bis[2-bromo-4-bis(2,3-epoxypropyl)aminophenyl]methane.

14. An epoxy compound as claimed in claim [11] *15* wherein the epoxy compound is bis[2-(trifluoromethyl)-4-bis(2,3-epoxypropyl)aminophenyl]methane.

15. An epoxy compound [as claimed in claim 1 wherein the epoxy compound includes two aromatic rings and two halogen or polyfluoroalkyl groups per aromatic ring, the epoxy compound] having the general formula:

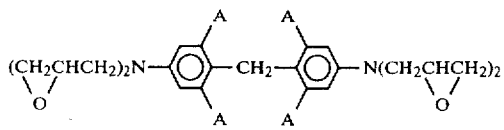

in which *each* A is a *group independently selected from hydrogen,* halogen [or] *and $A_1$, where $A_1$ represents a polyfluoroalkyl group $X(CF_2)_n$, where X is H or F and n is an integer in the range of 1 and 10, provided that at least one group A attached to each aromatic ring is halogen or $A_1$.*

20. An epoxy resing including a cured epoxy compound as claimed in claim [1] *15*.

21. An epoxy resin including a cured mixture of epoxy compounds including at least one epoxy compound as claimed in claim [1]*15*.

22. An epoxy resin including at least one cured epoxy compound as claimed in claim [1] *15* wherein the resin is a matrix of a fibre reinforced composite.

*23. An epoxy compound having a formula:*

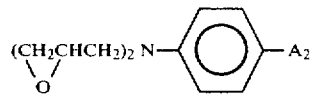

*wherein $A_2$ represents a polyfluoroalkoxy group $X(CF_2)_nCH_2O$, where X is H or F and n is an integer in the range from 1 to 10.*

*24. An epoxy compound as claimed in claim 7 wherein the groups A are identical groups $A_1$.*

*25. An epoxy compound as claimed in claim 7 wherein the compound is 3,5-bis(trifluoromethyl)-N,N-bis(2,3-epoxypropyl)aniline.*

*26. An epoxy resin including at least one cured epoxy compound, the epoxy compound being a compound as claimed in claim 7.*

*27. An epoxy resin including at least one cured epoxy compound, the epoxy compound being a compound as claimed in claim 23.*

* * * * *